US010308564B2

(12) United States Patent
Yang et al.

(10) Patent No.: US 10,308,564 B2
(45) Date of Patent: Jun. 4, 2019

(54) AROMATIC ALKYLATION USING CHEMICALLY-TREATED SOLID OXIDES

(71) Applicant: Chevron Phillips Chemical Company LP, The Woodlands, TX (US)

(72) Inventors: Qing Yang, Bartlesville, OK (US); Max P. McDaniel, Bartlesville, OK (US); Uriah J. Kilgore, Kingwood, TX (US); Mark L. Hlavinka, Tulsa, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/438,822

(22) Filed: Feb. 22, 2017

(65) Prior Publication Data
US 2017/0233309 A1 Aug. 17, 2017

Related U.S. Application Data

(63) Continuation of application No. 15/045,476, filed on Feb. 17, 2016, now Pat. No. 9,611,188.

(51) Int. Cl.
*C07C 2/68* (2006.01)
*C07C 2/66* (2006.01)
*B01J 21/12* (2006.01)
*B01J 27/10* (2006.01)
*B01J 27/12* (2006.01)
*B01J 37/24* (2006.01)
*B01J 37/26* (2006.01)
*B01J 27/053* (2006.01)
*B01J 37/02* (2006.01)

(52) U.S. Cl.
CPC .................. *C07C 2/68* (2013.01); *B01J 21/12* (2013.01); *B01J 27/053* (2013.01); *B01J 27/10* (2013.01); *B01J 27/12* (2013.01); *B01J 37/0201* (2013.01); *B01J 37/0209* (2013.01); *B01J 37/24* (2013.01); *B01J 37/26* (2013.01); *C07C 2/66* (2013.01); *C07C 2521/04* (2013.01); *C07C 2521/12* (2013.01); *C07C 2527/06* (2013.01); *C07C 2527/10* (2013.01); *C07C 2527/12* (2013.01); *C07C 2527/125* (2013.01)

(58) Field of Classification Search
CPC ................ C07C 2/66; C07C 2/68; C08F 4/42
See application file for complete search history.

(56) References Cited

U.S. PATENT DOCUMENTS

| 3,132,110 | A | * | 5/1964 | Hansford | ................. | B01J 21/04 423/544 |
|---|---|---|---|---|---|---|
| 3,275,702 | A | | 9/1966 | Hutson, Jr. | | |
| 3,365,509 | A | | 1/1968 | Shook | | |
| 3,717,586 | A | | 2/1973 | Suggitt et al. | | |
| 4,092,371 | A | | 5/1978 | Franck et al. | | |
| 4,806,513 | A | | 2/1989 | McDaniel et al. | | |
| 5,196,574 | A | | 3/1993 | Kocal | | |
| 5,770,782 | A | | 6/1998 | Knifton et al. | | |
| 5,777,187 | A | | 7/1998 | Knifton et al. | | |
| 5,847,254 | A | | 12/1998 | Knifton et al. | | |
| 6,107,230 | A | | 8/2000 | McDaniel et al. | | |
| 6,133,492 | A | | 10/2000 | Anantaneni | | |
| 6,165,929 | A | | 12/2000 | McDaniel et al. | | |
| 6,166,281 | A | | 12/2000 | Anantaneni | | |
| 6,294,494 | B1 | | 9/2001 | McDaniel et al. | | |
| 6,300,271 | B1 | | 10/2001 | McDaniel et al. | | |
| 6,316,553 | B1 | | 11/2001 | McDaniel et al. | | |
| 6,355,594 | B1 | | 3/2002 | McDaniel et al. | | |
| 6,376,415 | B1 | | 4/2002 | McDaniel et al. | | |
| 6,388,017 | B1 | | 5/2002 | McDaniel et al. | | |
| 6,391,816 | B1 | | 5/2002 | McDaniel et al. | | |
| 6,395,666 | B1 | | 5/2002 | McDaniel et al. | | |
| 6,524,987 | B1 | | 2/2003 | Collins et al. | | |
| 6,548,441 | B1 | | 4/2003 | McDaniel et al. | | |
| 6,548,442 | B1 | | 4/2003 | McDaniel et al. | | |
| 6,576,583 | B1 | | 6/2003 | McDaniel et al. | | |
| 6,613,712 | B1 | | 9/2003 | McDaniel et al. | | |
| 6,632,894 | B1 | | 10/2003 | McDaniel et al. | | |
| 6,667,274 | B1 | | 12/2003 | Hawley et al. | | |
| 6,750,302 | B1 | | 6/2004 | McDaniel et al. | | |
| 7,294,599 | B2 | | 11/2007 | Jensen et al. | | |
| 7,547,810 | B2 | * | 6/2009 | Boyer | ...................... | B01J 29/06 585/467 |
| 7,601,665 | B2 | | 10/2009 | McDaniel et al. | | |
| 7,884,163 | B2 | | 2/2011 | McDaniel et al. | | |
| 8,293,698 | B2 | * | 10/2012 | Le Coent | ............. | C10M 135/10 510/424 |
| 8,309,485 | B2 | | 11/2012 | Yang et al. | | |
| 8,623,973 | B1 | | 1/2014 | McDaniel et al. | | |

(Continued)

FOREIGN PATENT DOCUMENTS

| EP | 0 615 968 | 9/1994 |
|---|---|---|
| EP | 1 714 952 | 10/2006 |

OTHER PUBLICATIONS

International Search Report and the Written Opinion of the International Searching Authority in PCT/US2017/014024 dated Apr. 4, 2017, 9 pages.

(Continued)

*Primary Examiner* — Youngsul Jeong
(74) *Attorney, Agent, or Firm* — Merchant & Gould P.C.

(57) ABSTRACT

The present invention discloses processes for alkylating an aromatic compound, such as benzene or toluene, using a chemically-treated solid oxide. Suitable chemically-treated solid oxides include fluorided silica-coated alumina and fluorided-chlorided silica-coated alumina.

21 Claims, No Drawings

(56) References Cited

U.S. PATENT DOCUMENTS

| 8,703,886 B1 | 4/2014 | Yang et al. |
| 9,023,959 B2 | 5/2015 | McDaniel et al. |
| 9,611,188 B1 | 4/2017 | Yang et al. |
| 2015/0018503 A1 | 1/2015 | McDaniel et al. |

OTHER PUBLICATIONS

Michal et al., entitled "*Alkylation of Benzene with Linear 1-Alkenes in Liquid Phase. Influence of Zeolite Type and Chain Length of 1-Alkenes on the Activity and Selectivity*," $44^{th}$ International Petroleum Conference, Bratislava, Slovak Republic, Sep. 21-22, 2009, pp. 1-12.

Perego et al., entitled "*Recent advances in the industrial alkylation of aromatics: new catalysts and new processes*," Catalysis Today, 2002, vol. 73, pp. 3-22.

\* cited by examiner

AROMATIC ALKYLATION USING CHEMICALLY-TREATED SOLID OXIDES

This application is a continuation application of co-pending U.S. patent application Ser. No. 15/045,476, filed on Feb. 17, 2016, now U.S. Pat. No. 9,611,188, the disclosure of which is incorporated herein by reference in its entirety.

BACKGROUND OF THE INVENTION

The present invention relates generally to processes for alkylating an aromatic compound using a chemically-treated solid oxide. In certain alkylation processes provided herein, the chemically-treated solid oxide can comprise fluorided silica-coated alumina or fluorided-chlorided silica-coated alumina.

SUMMARY OF THE INVENTION

This summary is provided to introduce a selection of concepts in a simplified form that are further described herein. This summary is not intended to identify required or essential features of the claimed subject matter. Nor is this summary intended to be used to limit the scope of the claimed subject matter.

Processes for alkylating aromatic compounds are disclosed and described herein. Such processes can comprise contacting an aromatic compound, an olefin feedstock, and a chemically-treated solid oxide to produce a product comprising an alkylated aromatic compound. In some embodiments, the aromatic compound can comprise a $C_6$ to $C_{10}$ aromatic compound (for example, benzene or toluene, among other aromatic compounds), the olefin feedstock can comprise a $C_2$ to $C_{40}$ olefin (for example, a $C_2$ to $C_{24}$ alpha olefin or a $C_2$ to $C_{18}$ normal alpha olefin, among other olefin feedstocks), and the chemically-treated solid oxide can comprise a chemically-treated silica-coated alumina (for example, fluorided silica-coated alumina or fluorided-chlorided silica-coated alumina, among other chemically-treated solid oxides). These processes can provide unexpectedly high olefin conversions and alkylated aromatic selectivities at relatively low alkylation temperatures (for example, from 0 to 75° C., or from 20 to 60° C., among other alkylation temperatures).

The chemically-treated solid oxide used in the disclosed alkylation processes can contain a silica-coated alumina having a weight ratio of alumina to silica (alumina:silica) greater than or equal to 1.1:1, i.e., the silica-coated alumina is alumina-rich. Often, the alumina:silica ratio of the silica-coated alumina can range from 1.1:1 to 50:1, or from 1.2:1 to 6:1, among other alumina:silica ratios.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects and embodiments may be directed to various feature combinations and sub-combinations described in the detailed description.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects and/or embodiments, a combination of different features can be envisioned. For each and every aspect, and/or embodiment, and/or feature disclosed herein, all combinations that do not detrimentally affect the designs, compositions, processes, and/or methods described herein are contemplated with or without explicit description of the particular combination. Additionally, unless explicitly recited otherwise, any aspect, and/or embodiment, and/or feature disclosed herein can be combined to describe inventive features consistent with the present disclosure.

Regarding claim transitional terms or phrases, the transitional term "comprising," which is synonymous with "including," "containing," "having," or "characterized by," is open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristics of the claimed invention. A "consisting essentially of" claim occupies a middle ground between closed claims that are written in a "consisting of" format and fully open claims that are drafted in a "comprising" format. Absent an indication to the contrary, describing a composition or method as "consisting essentially of" is not to be construed as "comprising," but is intended to describe the recited element that includes materials or steps which do not significantly alter the composition or method to which the term is applied. For example, an olefin feedstock consisting essentially of a material A can include impurities typically present in a commercially produced or commercially available sample of the recited compound or composition. When a claim includes different features and/or feature classes (for example, a method step, olefin feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize an olefin feedstock consisting of specific components; alternatively, consisting essentially of specific components; or alternatively, comprising the specific components and other non-recited components. While compositions and methods are described in terms of "comprising" various components or steps, the compositions and methods can also "consist essentially of" or "consist of" the various components or steps, unless specifically stated otherwise. For example, a chemically-treated solid oxide consistent with certain embodiments of the present invention can comprise; alternatively, consist essentially of; or alternatively, consist of; a fluorided silica-coated alumina.

The terms "a," "an," and "the" are intended to include plural alternatives, e.g., at least one, unless otherwise specified. For instance, the disclosure of "an electron-withdrawing anion" is meant to encompass one, or combinations of more than one, electron-withdrawing anion (e.g., sulfate, chloride, fluoride, etc.), unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; a general reference to a butyl group includes an n-butyl group, a sec-butyl group, an iso-butyl group, and a t-butyl group; a general reference to cyclododecatriene includes all isomeric forms (e.g., trans,trans,cis-1,5,9-cyclododecatriene, and trans,trans,trans-1,5,9-cyclododecatriene, among other dodecatrienes); and a general reference to 2,3-pentanediol includes 2R,3R-pentanediol, 2S,3S-pentanediol, 2R,3S-pentanediol, and mixtures thereof.

The terms "contact product," "contacting," and the like, are used herein to describe compositions and methods wherein the components are contacted together in any order, in any manner, and for any length of time, unless otherwise specified. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, the term "contacting" is used herein to refer to materials which can be blended, mixed, slurried, dissolved, reacted, treated, or otherwise contacted in some other manner. Hence, "contacting" two or more components can result in a mixture, a reaction product, a reaction mixture, etc.

As used herein, the "weight hourly space velocity" or "WHSV" is the ratio of the flow rate of the olefin feedstock (in weight/mass of olefin feedstock per hour) which comes in contact with a given weight/mass of chemically-treated solid oxide. Herein, WHSV will have the units of g/g/hr, unless specifically indicated otherwise.

The term "hydrocarbon" whenever used in this specification and claims refers to a compound containing only carbon and hydrogen. The term "olefin" as used herein refers to a hydrocarbon that has at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system, unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s). The term "alpha olefin" as used herein refers to any olefin that has a double bond between the first and second carbon atom of a contiguous chain of carbon atoms. The term "alpha olefin" includes linear and branched alpha olefins and alpha olefins which have more than one non-aromatic carbon-carbon double bond, unless expressly stated otherwise. The term "normal alpha olefin" as used herein refers to a linear aliphatic hydrocarbon mono-olefin having a double bond between the first and second carbon atom.

An "aromatic compound" refers to a compound containing a cyclically conjugated moiety that follows the Hückel (4n+2) rule and containing (4n+2) pi-electrons, where n is an integer from 1 to about 5. Aromatic compounds can be monocyclic or polycyclic, unless otherwise specified. Non-limiting examples of aromatic compounds include benzene, naphthalene, and toluene, among others.

The terms "alkylation," "alkylating," and the like refer to processes which produce a product containing an alkylated aromatic compound, and such processes encompass product mixtures of mono-alkylated aromatic compounds and multi-alkylated aromatic compounds (e.g., di-alkylated, tri-alkylated, etc.). When characteristics of the product of an alkylation process are disclosed, this is meant to include all products made by the alkylation process, including alkylated aromatics and olefin oligomers (if any), but to exclude unreacted olefins and aromatic compounds (i.e., excludes residual unreacted olefins and aromatic compounds that may be present in the reaction product), unless otherwise specified. Moreover, if an inert solvent is used, characterization of the product of an alkylation process is also meant to exclude any inert solvent that may be present, unless otherwise specified.

A "mono-alkylated" aromatic compound refers to an aromatic compound in which one alkyl substituent (from an olefin reactant) is added to an aromatic compound in the alkylation process. This terminology is used regardless of the number of substituents present in the (reactant) aromatic compound. For instance, toluene (methyl-benzene) contains one alkyl substituent on the aromatic group, but if used as a reactant herein, a "mono-alkylated" aromatic compound produced therefrom would contain two alkyl substituents: the methyl substituent originally present in the aromatic compound (i.e., toluene), and one substituent resulting from the olefin reactant that reacts with the aromatic compound (i.e., toluene) in the alkylation reaction.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

The alkylation of an aromatic compound using a chemically-treated solid oxide is disclosed herein. Suitable chemically-treated solid oxides include fluorided solid oxides, for example, fluorided silica-coated alumina and fluorided-chlorided silica-coated alumina, among other fluorided solid oxides.

Aromatic Alkylation Processes

Embodiments of this invention are directed to processes for producing alkylated aromatic compounds. One such process for alkylating an aromatic compound can comprise (or consist essentially of, or consist of) contacting the aromatic compound, an olefin feedstock comprising an olefin, and a chemically-treated solid oxide to produce a product comprising the alkylated aromatic compound. Generally, the features of the processes (e.g., the aromatic compound, the olefin feedstock comprising the olefin (e.g., carbon number and/or olefin type, among other olefin features), the chemically-treated solid oxide, the alkylated aromatic compound, and the conditions under which the product comprising the alkylated aromatic compound is produced, among other features) are independently described herein and these features can be combined in any combination to further describe the disclosed alkylation processes. Moreover, additional process steps can be performed before, during, and/or after any of the steps of any of the processes disclosed herein, unless stated otherwise.

In some embodiments, the olefin feedstock can comprise, consist essentially of, of consist of, a $C_2$ to $C_{40}$ olefin. Moreover, the olefin feedstock can comprise, consist essentially of, or consist of, any single carbon number olefins from $C_2$ to $C_{40}$ (e.g., $C_6$ olefins) or any combination of different single carbon number olefins from $C_2$ to $C_{40}$ (e.g., $C_3$ to $C_6$ olefins, or $C_8$, $C_{10}$, and $C_{12}$ olefins, among other combinations). Olefin feedstocks and olefins are described herein and their features can be utilized without limitation to further describe the olefin feedstock and olefins which can be utilized in the alkylation processes.

In some embodiments, the aromatic compound can comprise, consist essentially of, of consist of, a $C_6$ to $C_{24}$ aromatic compound. Moreover, the aromatic compound can comprise, consist essentially of, or consist of, a hydrocarbon aromatic compound (e.g., benzene or toluene). Aromatic compounds are described herein and their features can be utilized without limitation to further describe the aromatic compounds which can be utilized in the alkylation processes.

In some embodiments, the alkylation process can utilize a single chemically-treated solid oxide, or alternatively, the process can utilize more than one chemically-treated solid oxide. Chemically-treated solid oxides are described herein and can be utilized without limitation in the alkylation processes described herein.

Consistent with embodiments of this invention, the alkylation process can include contacting the aromatic compound, the olefin feedstock, the chemically-treated solid oxide, and additional unrecited materials (e.g., an inert solvent or diluent, or a stabilizer, amongst other materials) to produce a product comprising an alkylated aromatic compound. In other embodiments, the alkylating process can consist essentially of contacting the aromatic compound, the olefin feedstock, and the chemically-treated solid oxide to produce a product comprising an alkylated aromatic compound or, alternatively, consist of contacting the aromatic compound, the olefin feedstock, and the chemically-treated solid oxide to produce a product comprising an alkylated aromatic compound.

Thus, the formation of the product comprising the alkylated aromatic compound can occur in the presence (or absence) of an inert solvent. The amount of any inert solvent used in addition to the disclosed olefin feedstock and the aromatic compound is not limited to any particular range. Such solvent, or combination of solvents, can be used, for example, as a flow modifier to alter the flow properties or viscosity of the reactants and/or the product during the alkylation process. Inert solvents which can be utilized are described herein, and these solvents can be utilized without limitation in the alkylation processes described herein. In an embodiment, the alkylation process can be performed in the substantial absence of an inert solvent (e.g., less than 10, 5, 4, 3, 2, or 1 wt. % solvent, based upon the total weight of the aromatic compound, the olefin feedstock, and the inert solvent).

The process for alkylating an aromatic compound can be conducted at a variety of temperatures, pressures, and time periods. For instance, the temperature at which the aromatic compound, the olefin feedstock, and the chemically-treated solid oxide are initially combined can be the same as, or different from, the temperature at which the product containing the alkylated aromatic compound is formed. As an illustrative example, the aromatic compound, the olefin feedstock, and the chemically-treated solid oxide can be initially charged or combined at temperature T1 and, after this initial charging of these materials, the temperature can be changed to a temperature T2 to allow for the alkylation reaction to proceed to form the product containing the alkylated aromatic compound. Likewise, the pressure can be varied throughout the process.

In an embodiment, the process for alkylating the aromatic compound can be conducted and/or the alkylated aromatic compound can be produced at any suitable alkylation temperature for the aromatic compound, the olefin feedstock, and the chemically-treated solid oxide. For instance, the process can be conducted and/or the alkylated aromatic compound can be produced at a minimum temperature of 0° C., 10° C., 15° C., or 20° C.; or alternatively, at a maximum temperature of 200° C., 150° C., 120° C., 100° C., 75° C., 60° C., or 50° C. In an embodiment, the alkylation temperature can be in a range from any minimum temperature disclosed herein to any maximum temperature disclosed herein. In some non-limiting embodiments, the alkylation temperature can be in a range from 0° C. to 200° C.; alternatively, from 0° C. to 150° C.; alternatively, from 0° C. to 100° C.; alternatively, from 0° C. to 75° C.; alternatively, from 0° C. to 60° C.; alternatively, from 0° C. to 50° C.; alternatively, from 20° C. to 150° C.; alternatively, from 20° C. to 100° C.; alternatively, from 20° C. to 75° C.; alternatively, from 20° C. to 60° C.; or alternatively, from 20° C. to 50° C. In other non-limiting embodiments, the process can be conducted and/or the alkylated aromatic compound can be produced at an alkylation temperature in a range from 10° C. to 60° C., from 10° C. to 50° C., from 15° C. to 75° C., or from 15° C. to 50° C. Other temperature ranges for the alkylation temperature are readily apparent from this disclosure. These temperature ranges also are meant to encompass circumstances where the alkylation process is conducted and/or the alkylated aromatic compound is produced at a series of different temperatures, instead of at a single fixed temperature, falling within the respective temperature ranges.

Generally, the alkylation process can be performed and/or the alkylated aromatic compound can be produced at any suitable pressure. For instance, the process can be conducted and/or the alkylated aromatic compound can be produced at a minimum pressure of 0 psig (0 kPa), 5 psig (34 kPa), or 10 psig (69 kPa); or alternatively, at a maximum pressure of 1000 psig (6,890 kPa), 750 psig (5,170 kPa), 500 psig (3,450 kPa), 250 psig (1,720 kPa), 150 psig (1,030 kPa), or 100 psig (689 kPa).

In an embodiment, the alkylation pressure can be in a range from any minimum pressure disclosed herein to any maximum pressure disclosed herein. While not being limited thereto, the process for alkylating an aromatic compound can be conducted and/or the alkylated aromatic compound can be produced at a reaction pressure in a range from 0 to 1000 psig (0 to 6,890 kPa), from 5 to 1000 psig (34 to 6,890 kPa), from 5 to 750 psig (34 to 5,170 kPa), from 5 to 500 psig (34 to 3,450 kPa), from 5 to 250 psig (34 to 1,720 kPa), from 5 to 150 psig (34 to 1,030 kPa), or from 10 to 100 psig (69 to 689 kPa). In some embodiments, the alkylation process can be conducted and/or the alkylated aromatic compound can be produced at atmospheric pressure, while in other embodiments, the alkylation process can be conducted and/or the alkylated aromatic compound can be produced at sub-atmospheric pressures. These pressure ranges also are meant to encompass circumstances where the alkylation process is conducted and/or the alkylated aromatic compound is produced at a series of different pressures, instead of at a single fixed pressure, falling within the respective pressure ranges.

In the alkylation process, the molar ratio of the aromatic compound to the olefin feedstock (aromatic:olefin) is not particularly limited. For instance, the process can be conducted and/or the alkylated aromatic compound can be produced at a minimum aromatic compound to olefin feedstock molar ratio of 0.2:1, 0.5:1, 0.7:1, 1:1, 2:1, 5:1, or 7:1; or alternatively, at a maximum aromatic compound to olefin feedstock molar ratio of 50:1, 35:1, 25:1, 17:1, 15:1, 10:1, 7:1, 5:1, 4:1, 3:1, or 2:1. In an embodiment, the aromatic compound to olefin feedstock molar ratio can be in a range from any minimum aromatic compound to olefin feedstock molar ratio disclosed herein to any maximum aromatic compound to olefin feedstock molar ratio disclosed herein, as long as the maximum aromatic compound to olefin feedstock molar ratio is greater than the minimum aromatic compound to olefin feedstock molar ratio. In some non-limiting embodiments, the molar ratio can be in a range from 0.2:1 to 50:1, from 0.5:1 to 50:1, from 1:1 to 50:1, from 2:1 to 35:1, or from 5:1 to 25:1. In embodiments wherein mono-alkylated aromatic compounds are desired, high molar ratios (aromatic:olefin) often can be used, such as in a non-limiting range from 5:1 to 20:1, from 5:1 to 15:1, or from 7:1 to 17:1. In embodiments wherein multi-alkylated aromatic compounds are desired, low molar ratios (aromatic:olefin) often can be used, such as in a non-limiting range from 0.2:1 to 5:1, from 0.5:1 to 4:1, from 0.5: to 2:1, or from 0.7:1 to 2:1. Other molar ratios of aromatic:olefin are readily apparent from this disclosure. As one of skill in the art would readily recognize, the aromatic:olefin molar ratio can change as the alkylation reaction proceeds. Accordingly, these ranges of aromatic:olefin molar ratios are meant to encompass the initial reactant ratio as well as any aromatic:olefin molar ratio encountered as the alkylation reaction proceeds.

In the alkylation process, the weight ratio of the olefin feedstock to the chemically-treated solid oxide is not particularly limited. For instance, the process can be conducted and/or the alkylated aromatic compound can be produced at a minimum olefin feedstock to chemically-treated solid oxide weight ratio of 1:1, 2:1, or 5:1; or alternatively, at a maximum olefin feedstock to chemically-treated solid oxide weight ratio of 1000:1, 750:1, 500:1, 250:1, or 100:1. In an embodiment, the olefin feedstock to chemically-treated solid oxide weight ratio can be in a range from any minimum olefin feedstock to chemically-treated solid oxide weight ratio disclosed herein to any maximum olefin feedstock to chemically-treated solid oxide weight ratio disclosed herein. In some non-limiting embodiments, the weight ratio can be in a range from 1:1 to 1000:1, from 1:1 to 100:1, or from 2:1 to 1000:1. In other embodiments, the weight ratio can be in a range from 2:1 to 100:1, from 5:1 to 1000:1, or from 5:1 to 100:1. Other weight ratios of the olefin feedstock to the chemically-treated solid oxide are readily apparent from this disclosure.

In one embodiment, the process for forming the alkylated aromatic compound can be a batch process. In another embodiment, the process for forming the alkylated aromatic compound can be a continuous process and/or a flow process. Further, the process for forming the alkylated aromatic compound can be a fixed bed process. In a fixed bed process, the olefin feedstock and chemically-treated solid oxide contact time (or reaction time) can be expressed in terms of weight hourly space velocity (WHSV), which is the ratio of the flow rate (g/hr) of the olefin feedstock into the fixed bed per unit weight (g) of the fixed bed of the chemically treated solid oxide. While not limited thereto, the WHSV employed for the process of producing a product containing the alkylated aromatic compound can have a minimum value of 0.05, 0.1, 0.25, 0.5, 0.75, or 1; or alternatively, a maximum value of 10, 5, 4, 3, 2.5, or 2. In an embodiment, the WHSV can be in a range from any minimum WHSV disclosed herein to any maximum WHSV disclosed herein. In a non-limiting example, the WHSV can be in a range from 0.05 to 10; alternatively, from 0.05 to 5; alternatively, from 0.05 to 4; alternatively, from 0.1 to 10; alternatively, from 0.1 to 5; alternatively, from 0.1 to 4; alternatively, from 0.1 to 3; alternatively, from 0.1 to 2; alternatively, from 0.1 to 1; alternatively, from 0.1 to 0.8; alternatively, from 0.5 to 10; alternatively, from 0.5 to 5; alternatively, from 0.5 to 4; alternatively, from 0.5 to 2.5; alternatively, from 0.8 to 3; or alternatively, from 1 to 3. Other suitable WHSV ranges are readily apparent from this disclosure.

The alkylation process can be conducted in any suitable reactor or vessel in order to form the product containing the alkylated aromatic compound, non-limiting examples of which can include a fixed bed reactor, a stirred tank reactor, a plug flow reactor, and a tubular reactor, including more than one reactor in series or in parallel, and including any combination of reactor types and arrangements. The alkylation process disclosed herein can be a batch process in some embodiments, while in other embodiments, the alkylation process can be a continuous process.

In an embodiment, the olefin feedstock conversion (or olefin conversion) is not particularly limited. The conversion of the olefin can be described as a "olefin conversion" to indicate that the percentage conversion, in mole percent, is based on the olefin and does not include non-olefin materials that can be present during the alkylation process, and is based on the moles of olefin consumed versus the moles of olefin initially present (as a reactant). Likewise, for example, the conversion of an olefin feedstock (or olefin conversion) comprising a $C_6$ olefin can be described as a "$C_6$ olefin conversion" to indicate that the percentage conversion, in mole percent, is based on the $C_6$ olefin and does not include non-$C_6$ olefin materials that can be present (e.g., other carbon number olefins) during the alkylation process. In another embodiment, the minimum olefin feedstock conversion (or olefin conversion) can be at least 10 mol %, at least 25 mol %, at least 50 mol %, at least 80 mol %, at least 90 mol %, at least 95 mol %, at least 98 mol %, or at least 99 mol %. In yet another embodiment, the maximum olefin feedstock conversion (or olefin conversion) can be 100 mol %, 99 mol %, 98 mol %, or 95 mol %. Generally, the olefin feedstock conversion (or olefin conversion) can be in a range from any minimum conversion disclosed herein to any maximum conversion disclosed herein. Non-limiting ranges of olefin feedstock conversion (or olefin conversion), in mole percentages, can include, but are not limited to, the following ranges: from 50 mol % to 100 mol %, from 80 mol % to 100 mol %, from 90 mol % to 100 mol %, from 95 mol % to 100 mol %, from 98 mol % to 100 mol %, from 99 mol % to 100 mol %, from 50 mol % to 99 mol %, from 50 mol % to 98 mol %, from 50 mol % to 95 mol %, from 80 mol % to 99 mol %, from 80 mol % to 98 mol %, from 50 mol % to 95 mol %, or from 90 mol % to 95 mol %. Other olefin feedstock conversion (or olefin conversion) ranges are readily apparent from this disclosure. In some embodiments, these conversions can be achieved in a batch process, while in other embodiments, these conversions can be achieved in a flow or continuous process, such as, for example, multi-passes thru a reactor, such as a fixed bed reactor. Yet, in other embodiments, these conversions can be achieved in a flow or continuous process, such as, for example, a single pass thru a reactor, such as a fixed bed reactor. In such embodiments, the conversions can be described as "single pass conversions" to indicate that the percentage conversions, in mole percent, are based on a single pass thru a reactor or reaction zone (e.g., a single pass $C_6$ olefin conversion).

In an alkylation process consistent with this invention in which the chemically-treated solid oxide comprises fluorided silica-coated alumina, unexpectedly, an olefin conversion (or single pass olefin conversion) can be greater than that of a comparable process using (silica-rich) fluorided silica-alumina (i.e., instead of fluorided silica-coated alumina), under the same alkylation conditions. In particular embodiments, the increase in conversion using fluorided silica-coated alumina instead of (silica-rich) fluorided silica-alumina can be at least 10%, at least 20%, at least 30%, at least 40%, at least 50%, at least 75%, or at least 100%, and often up to 150-200%. The percentage increases are based on the conversion using fluorided silica-alumina; for example, if the conversion using fluorided silica-alumina (in mole percentage) was 50% and the conversion using fluorided silica-coated alumina (in the same mole percentage basis) was 80%, then the percentage increase would be a 60% increase.

Similarly, in an alkylation process consistent with this invention in which the chemically-treated solid oxide comprises fluorided-chlorided silica-coated alumina, unexpectedly, an olefin conversion (or single pass olefin conversion) can be greater than that of a comparable process using (silica-rich) fluorided silica-alumina (i.e., instead of fluorided-chlorided silica-coated alumina), under the same alkylation conditions. In particular embodiments, the increase in conversion using fluorided-chlorided silica-coated alumina instead of (silica-rich) fluorided silica-alumina can be at least 10%, at least 20%, at least 30%, at least 40%, at least 50%, at least 75%, or at least 100%, and often up to 150-200%. As above, the percentage increases are based on the conversion using fluorided silica-alumina.

It is contemplated that the alkylation processes disclosed herein can have excellent selectivity to mono-alkylated aromatic compounds, as opposed to multi-alkylated aromatic compounds, e.g., di-alkylated compounds, tri-alkylated compounds, etc. In one embodiment, for example, the alkylation product can be characterized by a molar ratio of mono-alkylated aromatic compounds to multi-alkylated aromatic compounds (mono-alkylated:multi-alkylated) of at least 1:1, e.g., a mono-alkylated:multi-alkylated molar ratio of at least 1.1:1, at least 1.2:1, at least 1.5:1, at least 2:1, at least 3:1, at least 5:1, or at least 10:1. Illustrative and non-limiting ranges for the mono-alkylated:multi-alkylated molar ratio, therefore, can include from 1:1 to 50:1, from 1.1:1 to 50:1, from 1.2:1 to 50:1, from 2:1 to 50:1, from 3:1 to 50:1, from 5:1 to 50:1, from 10:1 to 50:1, from 1.1:1 to 25:1, from 1.2:1 to 25:1, from 1.5:1 to 25:1, from 2:1 to 25:1, from 3:1 to 25:1, from 5:1 to 25:1, or from 10:1 to 25:1. Other suitable ranges for the mono-alkylated:multi-alkylated molar ratio are readily apparent from this disclosure.

Additionally, it is contemplated that the alkylation processes disclosed herein can produce very low amounts of olefin oligomers. In one embodiment, the alkylation product can contain less than or equal to 10 wt. %, less than or equal to 8 wt. %, or less than or equal to 5 wt. %, olefin oligomers, based on the total weight of the product. In another embodiment, the alkylation product can contain less than or equal to 3 wt. %, less than or equal to 2 wt. %, less than or equal to 1 wt. %, less than or equal to 0.5 wt. %, less than or equal to 0.25 wt. %, or less than or equal to 0.1 wt. %, olefin oligomers, based on the total weight of the product. Other suitable amounts of the olefin oligomers are readily apparent from this disclosure.

While not intending to be bound by the following theory, it is believed that the excellent olefin conversions and selectivities to mono-alkylated aromatic compounds disclosed herein, as well as the minimal amounts of olefin oligomers produced in the alkylation process, can be more readily achieved at higher aromatic:olefin molar ratios, such as greater than 5:1, or greater than 7:1, with typical aromatic:olefin molar ratios falling within the range of 5:1 to 25:1, or 7:1 to 17:1.

Consistent with embodiments of this invention, the alkylated aromatic compound can be isolated from the product, as well as from residual reactants and the catalyst. For instance, any process disclosed herein can further comprise a step of separating at least a portion of the chemically-treated solid oxide from the alkylated aromatic compound. Additionally or alternatively, any process disclosed herein can further comprise a step of isolating at least a portion of the alkylated aromatic compound from the aromatic compound, and/or from the olefin feedstock, and/or from the chemically-treated solid oxide. As would be recognized by one of skill in the art, these steps can be performed using any suitable technique, such as filtration, evaporation, or distillation, as well as combinations of two or more of these techniques.

Olefin Feedstocks

Embodiments of this invention are directed to alkylation processes comprising contacting an aromatic compound, an olefin feedstock, and a chemically-treated solid oxide to produce a product comprising an alkylated aromatic compound. A wide range of olefin feedstocks comprising, consisting essentially of, or consisting of, $C_2$ to $C_{40}$ olefins can be utilized in the alkylation processes provided herein, and using the chemically-treated solid oxides and the aromatic compounds disclosed herein. In any embodiment, the olefin feedstock can comprise internal olefins and/or the olefin feedstock can comprise alpha olefins. In some embodiments, the internal olefins can comprise, or consist essentially of, linear olefins. Further, the alpha olefins can comprise, consist essentially of, or consist of, normal alpha olefins. Consequently, in some embodiments, the alkylation processes disclosed herein can employ an olefin feedstock which is a mixture of internal olefins and alpha olefins. In some embodiments, the olefin feedstock can comprise, or consist essentially of, alpha olefins; or alternatively, normal alpha olefins. In some embodiments, the olefins (internal olefins or alpha olefins) of the olefin feedstock can be mono-olefins.

Generally, the olefin feedstock can comprise (or consist essentially of, or consist of) a $C_2$ to $C_{40}$ olefin; alternatively, a $C_3$ to $C_{36}$ olefin; alternatively, a $C_3$ to $C_{24}$ olefin; or alternatively, a $C_3$ to $C_{18}$ olefin. In another embodiment, the olefin feedstock can comprise (or consist essentially of, or consist of) a $C_2$ to $C_{18}$ olefin; alternatively, a $C_3$ to $C_{18}$ olefin; alternatively, a $C_4$ to $C_{18}$ olefin; or alternatively, a $C_{18}$ to $C_{40}$ olefin. In yet another embodiment, the olefin feedstock can comprise a $C_2$ to $C_{18}$ olefin; alternatively, a $C_3$ to $C_8$ olefin; alternatively, a $C_4$ to $C_8$ olefin; alternatively, a $C_{10}$ to $C_{18}$ olefin; or alternatively, a $C_{10}$ to $C_{14}$ olefin. In other embodiments, the olefin feedstock can comprise (or consist essentially of, or consist of) a $C_2$ olefin; alternatively, a $C_3$ olefin; alternatively, a $C_4$ olefin; alternatively, a $C_5$ olefin; alternatively, a $C_6$ olefin; alternatively, a $C_7$ olefin; alternatively, a $C_8$ olefin; alternatively, a $C_{10}$ olefin; alternatively, a $C_{12}$ olefin; alternatively, a $C_{14}$ olefin; alternatively, a $C_{16}$ olefin; or alternatively, a $C_{18}$ olefin. Thus, mixtures of olefins having different numbers of carbon atoms can be used, or olefins having predominantly a single number of carbon atoms can be used as the olefin feedstock in the disclosed alkylation processes.

In an embodiment, the olefin feedstock can comprise at least 50 wt. %, at least 55 wt. %, at least 60 wt. %, at least 65 wt. %, at least 70 wt. %, at least 75 wt. %, at least 80 wt. %, at least 85 wt. %, at least 90 wt. %, at least 92.5 wt. %, or at least 95 wt. % of any olefin, olefin carbon number or carbon number range, or mixture of olefins described herein. Additionally or alternatively, the olefin feedstock can comprise a maximum of 100 wt. %, 99 wt. %, 98 wt. %, 97 wt. %, or 96 wt. %, of any olefin, olefin carbon number or carbon number range, or mixture of olefins described herein. Generally, the weight percent can be in a range from any minimum weight percent disclosed herein to any maximum weight percent disclosed herein. Therefore, non-limiting weight percent ranges can include, but are not limited to, the following ranges: from 50 to 100 wt. %, from 55 to 99 wt. %, from 60 to 98 wt. %, from 65 to 97 wt. %, from 70 to 96 wt. %, from 75 to 100 wt. %, from 80 to 100 wt. %, or from 80 to 98 wt. % of any olefin, olefin carbon number or carbon number range, or mixture of olefins described herein. Other weight percent ranges are readily apparent from this disclosure.

In these and other embodiments, the olefins can be cyclic or acyclic, and/or linear or branched. For example, the olefin feedstock can comprise, consist essentially of, or consist of, cyclic olefins; additionally or alternatively, the olefin feedstock can comprise, consist essentially of, or consist of, linear olefins. In other embodiments, the olefins of the olefin feedstock can comprise, or consist essentially of, aliphatic olefins. Moreover, the olefin feedstock can comprise olefins having only one olefin moiety (mono-olefins) and/or olefins having two olefin moieties (di-olefins), as well as compounds having more than two olefin moieties per molecule; alternatively, mono-olefins; alternatively, di-olefins; or alternatively, olefins having more than two olefin moieties per molecule.

The olefin feedstock can comprise linear and/or branched olefins, and therefore, mixtures of linear and branched olefins can be used. Suitable branched olefins can, for example, have a branch at any position and can have the double bond at any suitable position. In one embodiment, the branched olefin can have more than one branch. In another embodiment, the branched olefin can have one or more branches at the carbon-carbon double bond; or alternatively, the branched olefin can have one or more branches on carbon atoms that are not part of a carbon-carbon double bond. In yet another embodiment, the olefin feedstock can comprise, consist essentially of, or consist of, linear olefins; or alternatively, linear internal olefins.

In further embodiments, the olefin feedstock can comprise (or consist essentially of, or consist of) a $C_2$ to $C_{40}$ alpha olefin (or normal alpha olefin), alternatively, a $C_3$ to $C_{36}$ alpha olefin (or normal alpha olefin); alternatively, a $C_3$ to $C_{24}$ alpha olefin (or normal alpha olefin); or alternatively, a $C_3$ to $C_{18}$ alpha olefin (or normal alpha olefin). In another embodiment, the olefin feedstock can comprise (or consist essentially of, or consist of) a $C_2$ to $C_{18}$ alpha olefin (or normal alpha olefin); alternatively, a $C_3$ to $C_{18}$ alpha olefin (or normal alpha olefin); alternatively, a $C_4$ to $C_{18}$ alpha olefin (or normal alpha olefin); or alternatively, a $C_{18}$ to $C_{40}$ alpha olefin (or normal alpha olefin). In yet another embodiment, the olefin feedstock can comprise a $C_2$ to $C_{18}$ alpha olefin (or normal alpha olefin); alternatively, a $C_3$ to $C_8$ alpha olefin (or normal alpha olefin); alternatively, a $C_4$ to $C_8$ alpha olefin (or normal alpha olefin); alternatively, a $C_{10}$ to $C_{18}$ alpha olefin (or normal alpha olefin); or alternatively, a $C_{10}$ to $C_{14}$ alpha olefin (or normal alpha olefin). In other embodiments, the olefin feedstock can comprise (or consist essentially of, or consist of) ethylene, propylene, 1-butene, 1-pentene, 1-hexene, 1-octene, 1-decene, 1-dodecene, 1-tetradecene, 1-hexadecene, 1-octadecene, or any combination thereof; alternatively, ethylene, propylene, 1-butene, 1-pentene, or any combination thereof; alternatively, ethylene; alternatively, propylene; alternatively, 1-butene; or alternatively, 1-pentene. Yet, in other embodiments, the olefin feedstock can comprise (or consist essentially of, or consist of) 1-hexene, 1-octene, 1-decene, 1-dodecene, 1-tetradecene, 1-hexadecene, 1-octadecene, or any combination thereof; alternatively, 1-octene, 1-decene, 1-dodecene, or any combination thereof; alternatively, 1-hexene; alternatively, 1-octene; alternatively, 1-decene, alternatively, 1-dodecene; alternatively, 1-tetradecene; alternatively, 1-hexadecene; or alternatively, 1-octadecene. Thus, mixtures of alpha olefins (or normal alpha olefins) having different numbers of carbon atoms can be used, or alpha olefins (or normal alpha olefins) having predominantly a single number of carbon atoms can be used as the olefin feedstock in the disclosed alkylation processes.

Moreover, as above, the olefin feedstock can contain any suitable amount of any olefin, olefin carbon number range, or mixture of olefins described herein. For instance, the olefin feedstock can contain from 50 to 100 wt. %, from 55 to 99 wt. %, from 60 to 98 wt. %, from 65 to 97 wt. %, from 70 to 96 wt. %, from 75 to 100 wt. %, from 80 to 100 wt. %, or from 80 to 98 wt. % of a $C_2$ to $C_{40}$ linear internal olefin, alpha olefin, or normal alpha olefin; alternatively, linear internal olefins, alpha olefins, or normal alpha olefins of any carbon number range described herein; alternatively, of any combination of single carbon numbered linear internal olefins, alpha olefins, or normal alpha olefins described herein; or alternatively, of any single carbon numbered linear internal olefin, alpha olefin, or normal alpha olefin described herein. Additionally, other weight percent ranges are readily apparent from this disclosure. For instance, in a non-limiting example, the olefin feedstock can comprise can comprise at least 75 wt. %, at least 80 wt. %, at least 85 wt. %, at least 90 wt. %, or at least 95 wt. %, of ethylene; alternatively, propylene; alternatively, 1-butene; alternatively, 1-pentene; alternatively, 1-hexene; alternatively, 1-octene; alternatively, 1-decene; alternatively, 1-dodecene; alternatively, 1-tetradecene; alternatively, 1-hexadecene; or alternatively, 1-octadecene.

As described herein, the olefin feedstock can comprise various carbon number ranges and/or types of olefins. The various carbon number(s) of the olefin(s), the type of olefin(s), and the weight percentage of the olefin(s) can be combined in any fashion to describe the olefin feedstock or olefin(s) that are suitable for use in the alkylation processes of this invention.

Chemically-Treated Solid Oxides

In the alkylation processes disclosed herein, an aromatic compound, an olefin feedstock, and a chemically-treated solid oxide can be contacted to produce a product comprising an alkylated aromatic compound. Any suitable chemically-treated solid oxide can be employed in this invention, whether one chemically-treated solid oxide or a mixture or combination of two or more different chemically-treated solid oxides. In one embodiment, the chemically-treated solid oxide can comprise a solid oxide treated with an electron-withdrawing anion. Alternatively, in another embodiment, the chemically-treated solid oxide can comprise a solid oxide treated with an electron-withdrawing anion, the solid oxide containing a Lewis-acidic metal ion. Non-limiting examples of suitable chemically-treated solid oxides are disclosed in, for instance, U.S. Pat. Nos. 7,294,599, 7,601,665, 7,884,163, 8,309,485, 8,623,973, 8,703,886, and 9,023,959.

The solid oxide can encompass oxide materials such as alumina, "mixed oxides" thereof such as silica-alumina, coatings of one oxide on another, and combinations and mixtures thereof. The mixed oxides such as silica-alumina can be single or multiple chemical phases with more than one metal combined with oxygen to form the solid oxide. Examples of mixed oxides that can be used to form a chemically-treated solid oxide, either singly or in combination, can include, but are not limited to, silica-alumina, silica-titania, silica-zirconia, alumina-titania, alumina-zirconia, zinc-aluminate, alumina-boria, silica-boria, alumino-phosphate-silica, and titania-zirconia. The solid oxide used herein also can encompass oxide materials such as silica-coated alumina, as described in U.S. Pat. No. 7,884,163 (e.g., Sasol Siral® 28, Sasol Siral® 40, etc.)

Accordingly, in one embodiment, the solid oxide can comprise silica, alumina, silica-alumina, silica-coated alumina, aluminum phosphate, aluminophosphate, heteropolytungstate, titania, silica-titania, zirconia, silica-zirconia, magnesia, boria, zinc oxide, any mixed oxide thereof, or any combination thereof. In another embodiment, the solid oxide can comprise alumina, silica-alumina, silica-coated alumina, aluminum phosphate, aluminophosphate, heteropolytungstate, titania, silica-titania, zirconia, silica-zirconia, magnesia, boria, or zinc oxide, as well as any mixed oxide thereof, or any mixture thereof. The solid oxides contemplated herein can have any suitable surface area, pore volume, and particle size, as would be recognized by those of skill in the art. In another embodiment, the solid oxide can comprise silica, alumina, titania, zirconia, magnesia, boria, zinc oxide, any mixed oxide thereof, or any combination thereof. In yet another embodiment, the solid oxide can comprise silica-alumina, silica-coated alumina, silica-titania, silica-zirconia, alumina-boria, or any combination thereof. In still another embodiment, the solid oxide can comprise silica, alumina, silica-alumina, silica-coated alumina, or any mixture thereof; alternatively, silica; alternatively, alumina; alternatively, silica-alumina; or alternatively, silica-coated alumina.

The silica-coated alumina solid oxide materials which can be used in the alkylation processes often are alumina-rich, for instance, the weight ratio of alumina to silica (alumina:silica) in the silica-coated alumina can be in a range from 1.05:1 to 50:1, from 1.1:1 to 50:1, or from 1.2:1 to 50:1. In one embodiment, the weight ratio of alumina:silica in the silica-coated alumina can be in a range from 1.05:1 to 25:1; alternatively, from 1.05:1 to 12:1; alternatively, from 1.05:1 to 6:1; or alternatively, from 1.05:1 to 4:1. In another embodiment, the weight ratio of alumina:silica in the silica-coated alumina can be in a range from 1.1:1 to 25:1; alternatively, from 1.1:1 to 12:1; alternatively, from 1.1:1 to 7:1; or alternatively, from 1.1:1 to 3:1. In yet another embodiment, the weight ratio of alumina:silica in the silica-coated alumina can be in a range from 1.2:1 to 25:1; alternatively, from 1.2:1 to 12:1; alternatively, from 1.2:1 to 6:1; alternatively, from 1.2:1 to 4:1; or alternatively, from 1.2:1 to 3:1. In still another embodiment, the weight ratio of alumina:silica in the silica-coated alumina can be in a range from 1.3:1 to 25:1; alternatively, from 1.3:1 to 12:1; alternatively, from 1.3:1 to 6:1; alternatively, from 1.3:1 to 4:1; or alternatively, from 1.3:1 to 3:1.

The electron-withdrawing component used to treat the solid oxide can be any component that can increase the Lewis or Brønsted acidity of the solid oxide upon treatment (as compared to the solid oxide that is not treated with at least one electron-withdrawing anion). According to one embodiment, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, tungstate, and molybdate, including mixtures and combinations thereof. In addition, other ionic or non-ionic compounds that serve as sources for these electron-withdrawing anions also can be employed. It is contemplated that the electron-withdrawing anion can be, or can comprise, fluoride, chloride, bromide, phosphate, triflate, bisulfate, or sulfate, or any combination thereof, in some embodiments provided herein. In other embodiments, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, or combinations thereof. Yet, in other embodiments, the electron-withdrawing anion can comprise sulfate, fluoride, chloride, or combinations thereof; alternatively, sulfate; alternatively, fluoride and chloride; or alternatively, fluoride.

The chemically-treated solid oxide generally can contain from 1 to 30 wt. % of the electron-withdrawing anion, based on the weight of the chemically-treated solid oxide. In particular embodiments provided herein, the chemically-treated solid oxide can contain from 1 to 20 wt. %, from 2 to 20 wt. %, from 3 to 20 wt. %, from 2 to 15 wt. %, from 3 to 15 wt. %, from 3 to 12 wt. %, from 4 to 10 wt. %, or from 5 to 9 wt. %, of the electron-withdrawing anion, based on the total weight of the chemically-treated solid oxide.

In an embodiment, the chemically-treated solid oxide can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, or phosphated silica-coated alumina, as well as any mixture or combination thereof. In another embodiment, the chemically-treated solid oxide employed in the alkylation processes described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, fluorided-chlorided silica-coated alumina, or sulfated silica-coated alumina, as well as combinations thereof. In yet another embodiment, the chemically-treated solid oxide can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; alternatively, fluorided-chlorided silica-coated alumina; or alternatively, fluorided silica-coated alumina. In some embodiments, the chemically-treated solid oxide can comprise a fluorided solid oxide, while in other embodiments, the chemically-treated solid oxide can comprise a sulfated solid oxide.

Various processes can be used to form chemically-treated solid oxides useful in the present invention. Methods of contacting the solid oxide with the electron-withdrawing component, suitable electron withdrawing components and addition amounts, impregnation with metals or metal ions (e.g., zinc, nickel, vanadium, titanium, silver, copper, gallium, tin, tungsten, molybdenum, zirconium, or combinations thereof), various calcining procedures and conditions, such as calcining temperatures (e.g., calcination temperatures in a range from 300° C. to 900° C., from 400° C. to 800° C., or from 500° C. to 700° C.), calcination times (e.g., calcination times in a range from 1 minute to 24 hours, from 5 minutes to 10 hours, or from 20 minutes to 6 hours), calcination equipment (e.g., calcination equipment such as a rotary kiln, muffle furnace, or fluidized bed, among other methods of conveying heat), and calcination atmospheres (e.g., dry or humid calcination atmospheres, oxidizing calcination atmospheres such as air or oxygen, reducing calcination atmospheres such as carbon monoxide or hydrogen, or non-reactive calcination atmospheres like nitrogen, argon or vacuum) are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485. Other suitable processes and procedures for preparing chemically-treated solid oxides (e.g., chemically-treated silica-coated aluminas, such as fluorided silica-coated alumina) are well known to those of skill in the art.

Aromatic Compounds and Alkylated Aromatics

In the alkylation processes disclosed herein, an aromatic compound, an olefin feedstock, and a chemically-treated solid oxide can be contacted to produce a product comprising an alkylated aromatic compound. Any suitable aromatic compound can be employed in this invention, whether one aromatic compound or a mixture or combination of two or more different aromatic compounds. For instance, the aromatic compound can comprise, consist essentially of, or consist of, a hydrocarbon aromatic compound.

Generally, the aromatic compound can comprise (or consist essentially of, or consist of) a $C_6$ to $C_{24}$ hydrocarbon aromatic compound. In another embodiment, the aromatic compound can comprise (or consist essentially of, or consist of) a $C_6$ to $C_{18}$, a $C_6$ to $C_{15}$, a $C_6$ to $C_{12}$, a $C_6$ to $C_{10}$, or a $C_6$ to $C_8$ hydrocarbon aromatic compound.

Illustrative and non-limiting examples of suitable hydrocarbon aromatic compounds include benzene, naphthalene, and their substituted analogues, as well as any combination thereof. In an embodiment, the hydrocarbon aromatic compound can be an alkylbenzene compound (e.g., toluene, cumene, xylene, ethylbenzene, and the like, as well as any combination thereof). In some embodiments, the aromatic compound can comprise (or consist essentially of, or consist of) benzene, napthalene, toluene, cumene, xylene, ethylbenzene, or any combination thereof; alternatively, benzene, toluene, cumene, xylene, ethylbenzene, or any combination thereof; alternatively, toluene, cumene, xylene, ethylbenzene, or any combination thereof; alternatively, benzene; alternatively, naphthalene; alternatively, toluene, xylene, or any combination thereof; alternatively toluene; alternatively, xylene; or alternatively, ethylbenzene.

The alkylated aromatic compounds encompassed herein can include any alkylated aromatic compound that can be produced using any aromatic compound disclosed herein and any olefin feedstock disclosed herein. For instance, $C_7$ to $C_{36}$, $C_7$ to $C_{24}$, $C_7$ to $C_{18}$, or $C_7$ to $C_{12}$, $C_7$ to $C_{10}$ alkylbenzene compounds (e.g., mono-alkylbenzene compounds, di-alkylbenzene compounds) can be produced herein.

Solvents

Suitable inert solvents that can be utilized in the processes disclosed herein include solvents that do not react with the olefin feedstocks, olefins, aromatic compounds, alkylated aromatic compounds, and chemically-treated solid oxide disclosed herein. Illustrative solvents can include, for example, saturated aliphatic hydrocarbons, such as saturated $C_3$ to $C_{20}$ aliphatic hydrocarbons; alternatively, saturated $C_4$ to $C_{15}$ aliphatic hydrocarbons; or alternatively, saturated $C_5$ to $C_{10}$ aliphatic hydrocarbons. The saturated aliphatic hydrocarbons can be cyclic or acyclic and/or can be linear or branched, unless otherwise specified.

Non-limiting examples of suitable acyclic aliphatic hydrocarbon solvents that can be utilized singly or in any combination include pentane (n-pentane or a mixture of saturated linear and branched $C_5$ acyclic aliphatic hydrocarbons), hexane (n-hexane or mixture of saturated linear and branched $C_6$ acyclic aliphatic hydrocarbons), heptane (n-heptane or mixture of saturated linear and branched $C_7$ acyclic aliphatic hydrocarbons), octane (n-octane or a mixture of saturated linear and branched $C_8$ acyclic aliphatic hydrocarbons), and combinations thereof; alternatively, pentane (n-pentane or a mixture of saturated linear and branched $C_5$ acyclic aliphatic hydrocarbons), hexane (n-hexane or mixture of saturated linear and branched $C_6$ acyclic aliphatic hydrocarbons), heptane (n-heptane or mixture of saturated linear and branched $C_7$ acyclic aliphatic hydrocarbons), octane (n-octane or a mixture of saturated linear and branched $C_8$ acyclic aliphatic hydrocarbons), and combinations thereof; hexane (n-hexane or a mixture of saturated linear and branched $C_6$ acyclic aliphatic hydrocarbons), heptane (n-heptane or mixture of saturated linear and branched $C_7$ acyclic aliphatic hydrocarbons), octane (n-octane or a mixture of saturated linear and branched $C_8$ acyclic aliphatic hydrocarbons), and combinations thereof; alternatively, pentane (n-pentane or a mixture of saturated linear and branched $C_5$ acyclic aliphatic hydrocarbons); alternatively, hexane (n-hexane or mixture of saturated linear and branched $C_6$ acyclic aliphatic hydrocarbons); alternatively, heptane (n-heptane or mixture of saturated linear and branched $C_7$ acyclic aliphatic hydrocarbons); or alternatively, octane (n-octane or a mixture of saturated linear and branched $C_8$ acyclic aliphatic hydrocarbons).

Non-limiting examples of suitable cyclic aliphatic hydrocarbon solvents include cyclohexane, methyl cyclohexane, and combinations thereof; alternatively cyclohexane; or alternatively, methylcyclohexane.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Chemically-Treated Solid Oxide Preparation

Example 1 utilized an untreated alumina, Alumina A from W. R. Grace, having a surface area of about 300 $m^2/g$ and a pore volume of about 1.2 mL/g.

Silica-coated aluminas were prepared as follows. The same alumina (Alumina A) used in Example 1 was first calcined at about 600° C. for approximately 6 hours, cooled to ambient temperature, and then contacted with tetraethylorthosilicate in isopropanol to equal 25 wt. % $SiO_2$. After drying, the silica-coated alumina was calcined at 600° C. for 3 hours. Fluorided silica-coated alumina (7 wt. % F) was prepared by impregnating the calcined silica-coated alumina with an ammonium bifluoride solution in methanol, drying, and then calcining for 3 hours at 600° C. in dry air. Afterward, the fluorided silica-coated alumina was collected and stored under dry nitrogen, and was used without exposure to the atmosphere.

Fluorided-chlorided silica-coated aluminas (4 wt. % Cl+7 wt. % F) were produced by first calcining the silica-coated alumina at 600° C. for 3 hours. The chloriding step involved injecting and vaporizing $CCl_4$ into an air stream (typically, over a time period of less than about 5 minutes) used to fluidize the silica-coated alumina during calcination at a peak chloriding temperature of 500° C. (total duration of the calcining operation was 4 hours). The fluoriding step involved injecting and vaporizing tetrafluoroethane into the air stream (typically, over a time period of less than about 5 minutes) used to fluidize the chlorided silica-coated alumina during calcination at a peak fluoriding temperature of 500° C. (total duration of the calcining operation was 4.5 hours).

Aromatic Alkylations

Gas chromatographic (GC) analyses were performed using a split injection method on a Varian CP-3800 gas chromatograph with a flame ionization detector (FID) and mass spectrometer detector (MS). Initial oven temperature was 70° C. for 2 minutes and increased 20° C./min to 250° C., then held at 250° C. for 49 minutes. The column was a CP8944 column, 30 m×0.25 mm×0.25 μm.

Examples 1-4

Alkylation of Toluene with 1-Hexene Using Different Chemically-Treated Solid Oxides In a drybox under a $N_2$ atmosphere, a glass vial was charged with alumina or a chemically-treated solid oxide, toluene, and 1-hexene. The glass vial was sealed and the mixture was stirred at either 5° C. (in a water-ice bath) or 25° C. (room temperature), for a set reaction time. The reaction was exothermic, and for Examples 2 and 4, the reaction temperature increased from room temperature to approximately 50° C. Table IA summarizes the reaction conditions for Examples 1-4. Example 1 used alumina, Examples 2-3 used fluorided silica-coated alumina (F-SCA), and Example 4 used fluorided/chlorided silica-coated alumina (F/Cl-SCA).

The contents of the glass vial were filtered to isolate the liquid product from the solid catalyst. A sample of this liquid product was then analyzed by gas chromatography to determine the composition of the reaction product. Table IB provides the compositional make-up of the reaction product. As shown in Table IB, no reaction was detected for Example 1, while Examples 2-4 produced alkylated toluene products, and with very low levels of olefin oligomers. Examples 2-4 had surprisingly high selectivities to the mono-alkylated toluene product, with weight ratios of mono-alkylated:multi-alkylated ranging from 1.5:1 to 2.6:1.

Example 5

Alkylation of Toluene with Propylene Using Fluorided Silica-Coated Alumina (F-SCA)

In a drybox under a $N_2$ atmosphere, a 500-mL glass reactor vessel was charged with 500 mg of fluorided silica-coated alumina (F-SCA). The reactor was assembled and removed from the drybox. The reactor was placed in an oil bath containing a water-filled cooling coil. Approximately 220 mL of dry toluene were added to the reactor. The vessel was then placed under 40 psig (275 kPa) of propylene. The reactor was mechanically stirred by an overhead stirrer. The initial temperature of the bath was 24° C. and the internal reactor temperature was 26° C. The internal reactor temperature rose to 75° C. within 5 minutes. The reactor pressure was allowed to fall to 5 psig (34.5 kPa) by consumption of propylene. The pressure was increased to 40 psig (275 kPa) and the propylene was consumed until the reactor pressure was 5 psig (34.5 kPa). This cycle was continuously repeated for forty minutes, never allowing the reactor temperature to reach 80° C. At this time, the internal reactor temperature stopped increasing with propylene feed. The reactor was then placed under a constant propylene pressure of 40 psig (275 kPa) for 20 minutes. Table IIA summarizes the reaction conditions for Example 5.

Propylene was removed from the reactor vessel, and the contents of the reactor vessel were filtered to isolate the liquid product from the solid catalyst. A sample of this liquid product was then analyzed by gas chromatography to determine the composition of the reaction product. Table IIB provides the compositional make-up of the reaction product. As shown in Table IIB, no olefin oligomers were detected, and Example 5 had a surprisingly high selectivity to the mono-alkylated toluene product, with a weight ratio of mono-alkylated:multi-alkylated of 1.1:1.

Example 6

Alkylation of Toluene with 1-Hexene Using Fluorided Silica-Coated Alumina (F-SCA)

Example 6 was performed similarly to Example 2, but with a toluene:1-hexene (aromatic:olefin) molar ratio of approximately 10:1. As with Example 2, the reaction temperature for Example 6 increased from room temperature to approximately 50° C. Table IIIA summarizes the reaction conditions for Example 6.

Table IIIB provides the compositional make-up of the reaction product. As shown in Table IIIB and unexpectedly, all of the 1-hexene was consumed (100% olefin conversion) and no olefin oligomers were detected. Example 6 had a surprisingly high selectivity to the mono-alkylated toluene product, with a weight ratio of mono-alkylated:multi-alkylated of about 12:1.

Examples 7-8

Alkylation of Toluene with 1-Dodecene Using Fluorided Silica-Coated Alumina (F-SCA)

In a drybox under a $N_2$ atmosphere, a glass vial was charged with F-SCA, toluene, and 1-dodecene. The glass vial was sealed and the mixture was stirred at 25° C. for a set reaction time. The reaction was exothermic, and for Examples 7-8, the reaction temperature increased from room temperature to approximately 45 to 50° C. Table IVA summarizes the reaction conditions for Examples 7-8. The main difference between Example 7 and Example 8 was the relative amounts of toluene and 1-dodecene, i.e., the aromatic:olefin molar ratio.

The contents of the glass vial were filtered to isolate the liquid product from the solid catalyst. A sample of this liquid product was then analyzed by gas chromatography to determine the composition of the reaction product. Table IVB provides the compositional make-up of the reaction product. As shown in Table IVB and unexpectedly, all of the 1-dodecene was consumed (100% olefin conversion) and no olefin oligomers were detected in Example 8, while the reaction product of Example 7 contained a very low level of olefin oligomers. Both Examples 7-8 had surprisingly high selectivities to the mono-alkylated toluene product, with a weight ratio of mono-alkylated:multi-alkylated of about 1.6:1 for Example 7 and about 12:1 for Example 8.

Comparison of Examples 2 and 6-8

Product Selectivity Based on Aromatic:Olefin Molar Ratio

Table V illustrates the surprising impact of the aromatic:olefin molar ratio on the selectivity to the mono-alkylated product when using a chemically-treated solid oxide catalyst (F-SCA). As shown by Examples 2 and 6, an increase in toluene:1-hexene (aromatic:olefin) molar ratio from 1.2:1 to 10.4:1 resulted in an increase in selectivity to the mono-alkylated toluene product, with the molar ratio of mono-alkylated:multi-alkylated increasing from 3.2:1 to 17:1. Likewise, as shown by Examples 7 and 8, an increase in toluene:1-dodecene (aromatic:olefin) molar ratio from 1.2:1 to 12.5:1 resulted in an increase in selectivity to the mono-alkylated toluene product, with the molar ratio of mono-alkylated:multi-alkylated increasing from 2.7:1 to 19:1.

TABLE IA

Examples 1-4 - Reaction conditions.

| Example | Catalyst Type | Catalyst (mg) | Toluene (mmol) | 1-Hexene (mmol) | Initial Temperature (° C.) | Reaction time (hr) |
|---|---|---|---|---|---|---|
| 1 | Alumina | 340 | 38 | 32 | 25 | 20 |
| 2 | F-SCA | 320 | 38 | 32 | 25 | 1 |
| 3 | F-SCA | 850 | 141 | 121 | 5 | 0.83 |
| 4 | F/Cl-SCA | 160 | 38 | 32 | 25 | 0.33 |

TABLE IB

Examples 1-4 - Product composition.

| | Product composition | | | | | | |
|---|---|---|---|---|---|---|---|
| Example | 1-Hexene (wt. %) | Toluene (wt. %) | Mono-alkylation Product (wt. %) | Di-alkylation Product (wt. %) | Tri-alkylation Product (wt. %) | Hexene Dimer (wt. %) | Hexene Trimer (wt. %) |
| 1 | No reaction was detected | | | | | | |
| 2 | 16.31 | 44.67 | 26.24 | 9.80 | 2.78 | 0.14 | 0.07 |
| 3 | 23.58 | 47.27 | 20.74 | 5.72 | 2.21 | 0.23 | 0.25 |
| 4 | 9.13 | 32.01 | 34.89 | 18.87 | 4.08 | 0.73 | 0.29 |

TABLE IIA

Example 5 - Reaction conditions.

| | Reaction conditions | | | | | |
|---|---|---|---|---|---|---|
| Example | Catalyst Type | Catalyst (mg) | Toluene (mL) | Propylene (psig) | Initial Temperature (° C.) | Reaction Time (hr) |
| 5 | F-SCA | 500 | 220 | 5-40 | 25 | 1 |

TABLE IIB

Example 5 - Product composition.

| | Product composition | | | | | | |
|---|---|---|---|---|---|---|---|
| Example | Liquid product (g) | Toluene (wt. %) | Mono-alkylation Product (wt. %) | Di-alkylation Product (wt. %) | Tri-alkylation Product (wt. %) | Propylene Dimer (wt. %) | Propylene Trimer (wt. %) |
| 5 | 243 | 39.09 | 32.06 | 19.05 | 9.79 | not detected | not detected |

TABLE IIIA

Example 6 - Reaction conditions.

| | Reaction conditions | | | | | |
|---|---|---|---|---|---|---|
| Example | Catalyst Type | Catalyst (mg) | Toluene (mmol) | 1-Hexene (mmol) | Initial Temperature (° C.) | Reaction Time (hr) |
| 6 | F-SCA | 220 | 84.6 | 8.1 | 25 | 1 |

TABLE IIIB

Example 6 - Product composition.

| | Product composition | | | | | | |
|---|---|---|---|---|---|---|---|
| Example | 1-Hexene (wt. %) | Toluene (wt. %) | Mono-alkylation Product (wt. %) | Di-alkylation Product (wt. %) | Tri-alkylation Product (wt. %) | Hexene Dimer (wt. %) | Hexene Trimer (wt. %) |
| 6 | 0.00 | 89.26 | 9.90 | 0.80 | 0.04 | not detected | not detected |

TABLE IVA

Examples 7-8 - Reaction conditions.

| | Reaction conditions | | | | | |
|---|---|---|---|---|---|---|
| Example | Catalyst Type | Catalyst (mg) | Toluene (mL) | 1-Dodecene (mmol) | Initial Temperature (° C.) | Reaction Time (hr) |
| 7 | F-SCA | 300 | 28.2 | 22.6 | 25 | 1.2 |
| 8 | F-SCA | 260 | 56.4 | 4.5 | 25 | 1.2 |

TABLE IVB

Examples 7-8 - Product composition.

| Example | 1-Dodecene (wt. %) | Toluene (wt. %) | Mono-alkylation Product (wt. %) | Di-alkylation Product (wt. %) | Tri-alkylation Product (wt. %) | Dodecene Dimer (wt. %) | Dodecene Trimer (wt. %) |
|---|---|---|---|---|---|---|---|
| 7 | 15.0 | 29.7 | 31.0 | 19.1 | 0 | 5.3 | 0.0 |
| 8 | 0 | 80.5 | 18.0 | 1.5 | 0 | not detected | not detected |

TABLE V

Selectivity Comparison.

| Example | 1-Olefin | Aromatic/Olefin Ratio (molar) | Mono/Di Ratio (weight) | Di/Tri Ratio (weight) | Mono/Di/Tri Addition Product Ratio (weight) | Mono/Multi Ratio (molar) | Mono/Di Ratio (molar) | Di/Tri Ratio (molar) | Mono/Di/Tri Addition Product Ratio (molar) |
|---|---|---|---|---|---|---|---|---|---|
| 2 | 1-Hexene | 1.2 | 2.7 | 3.5 | 9.5/3.5/1 | 3.2 | 4.0 | 4.7 | 18.4/4.7/1 |
| 6 | 1-Hexene | 10.4 | 12.4 | 20.0 | 248/20/1 | 17 | 17.9 | 27.7 | 496/28/1 |
| 7 | 1-Dodecene | 1.2 | 1.6 | N/A | N/A | 2.7 | 2.7 | N/A | N/A |
| 8 | 1-Dodecene | 12.5 | 12.0 | N/A | N/A | 19:1 | 19.1 | N/A | N/A |

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments are described as "comprising" but, alternatively, can "consist essentially of" or "consist of"):

Embodiment 1

A process for alkylating an aromatic compound, the process comprising: contacting the aromatic compound, an olefin feedstock, and a chemically-treated solid oxide to produce a product comprising an alkylated aromatic compound.

Embodiment 2

The process defined in embodiment 1, wherein the aromatic compound comprises a hydrocarbon aromatic compound.

Embodiment 3

The process defined in embodiment 1, wherein the aromatic compound comprises any number of carbon atoms disclosed herein, e.g., a $C_6$ to $C_{24}$ hydrocarbon aromatic compound, among others.

Embodiment 4

The process defined in embodiment 1, wherein the aromatic compound comprises any hydrocarbon aromatic compound disclosed herein, e.g., benzene, naphthalene, an alkylbenzene compound, or any combination thereof.

Embodiment 5

The process defined in embodiment 4, wherein the alkylbenzene compound comprises toluene, cumene, xylene, ethylbenzene, or any combination thereof.

Embodiment 6

The process defined in any one of embodiments 1-5, wherein the olefin feedstock comprises any olefin described herein, e.g., a mono-olefin, a di-olefin, a tri-olefin, or any combination thereof.

Embodiment 7

The process defined in any one of embodiments 1-6, wherein the olefin feedstock comprises any number of carbon atoms disclosed herein, e.g., a $C_2$ to $C_{40}$ olefin, a $C_3$ to $C_{24}$ olefin, or a $C_4$ to $C_{18}$ olefin.

Embodiment 8

The process defined in any one of embodiments 1-6, wherein the olefin feedstock comprises any alpha olefin described herein, e.g., a $C_2$ to $C_{40}$ alpha olefin, a $C_3$ to $C_{24}$ alpha olefin, or a $C_4$ to $C_{18}$ alpha olefin.

Embodiment 9

The process defined in any one of embodiments 1-6, wherein the olefin feedstock comprises any normal alpha olefin described herein, e.g., a $C_2$ to $C_{40}$ normal alpha olefin, a $C_3$ to $C_{24}$ normal alpha olefin, or a $C_4$ to $C_{18}$ normal alpha olefin.

Embodiment 10

The process defined in any one of embodiments 1-6, wherein the olefin feedstock comprises ethylene, propylene, 1-butene, 1-pentene, 1-hexene, 1-octene, 1-decene, 1-dodecene, 1-tetradecene, 1-hexadecene, 1-octadecene, or any combination thereof.

Embodiment 11

The process defined in any one of embodiments 1-10, wherein the chemically-treated solid oxide comprises a solid oxide treated with an electron-withdrawing anion, e.g., any solid oxide disclosed herein and any electron-withdrawing anion disclosed herein.

Embodiment 12

The process defined in embodiment 11, wherein (a) the solid oxide comprises silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof, and (b) the electron-withdrawing anion comprises sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or any combination thereof.

Embodiment 13

The process defined in embodiment 11 or 12, wherein the solid oxide comprises silica-coated alumina.

Embodiment 14

The process defined in any one of embodiments 11-13, wherein the electron-withdrawing anion comprises sulfate, fluoride, chloride, or any combination thereof.

Embodiment 15

The process defined in any one of embodiments 11-13, wherein the electron-withdrawing anion comprises sulfate.

Embodiment 16

The process defined in any one of embodiments 11-13, wherein the electron-withdrawing anion comprises fluoride, chloride, or both.

Embodiment 17

The process defined in any one of embodiments 1-10, wherein the chemically-treated solid oxide comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof.

Embodiment 18

The process defined in any one of embodiments 1-10, wherein the chemically-treated solid oxide comprises fluorided silica-coated alumina.

Embodiment 19

The process defined in any one of embodiments 1-10, wherein the chemically-treated solid oxide comprises fluorided-chlorided silica-coated alumina.

Embodiment 20

The process defined in any one of embodiments 11-19, wherein the weight percentage of the electron-withdrawing anion, based on the weight of the chemically-treated solid oxide, is in any range of weight percentages disclosed herein, e.g., from 1 to 30 wt. %, from 2 to 20 wt. %, from 3 to 15 wt. %, from 4 to 10 wt. %, or from 5 to 9 wt. %.

Embodiment 21

The process defined in any one of embodiments 1-20, wherein the chemically-treated solid oxide is produced by a process comprising calcining the chemically-treated solid oxide at any conditions disclosed herein, e.g., at a temperature from 300° C. to 750° C., from 500° C. to 700° C., or from 575° C. to 675° C.

Embodiment 22

The process defined in any one of embodiments 1-21, wherein the chemically-treated solid oxide comprises silica-coated alumina having a weight ratio of alumina to silica (alumina:silica) in any range disclosed herein, e.g., from 1.1:1 to 50:1, from 1.2:1 to 50:1, from 1.2:1 to 25:1, from 1.1:1 to 12:1, from 1.2:1 to 12:1, from 1.1:1 to 7:1, from 1.2:1 to 6:1, or from 1.2:1 to 4:1.

Embodiment 23

The process defined in any one of embodiments 1-22, wherein the alkylated aromatic compound is produced at an alkylation temperature in any range disclosed herein, e.g., from 0° C. to 200° C., from 0° C. to 150° C., from 0° C. to 75° C., from 0° C. to 60° C., from 0° C. to 50° C., from 20° C. to 200° C., from 20° C. to 150° C., from 20° C. to 75° C., from 20° C. to 60° C., or from 20° C. to 50° C.

Embodiment 24

The process defined in any one of embodiments 1-23, wherein the process is conducted in any reactor disclosed herein, e.g., a fixed bed reactor, a stirred tank reactor, a plug flow reactor, a tubular reactor, or any combination thereof.

Embodiment 25

The process defined in any one of embodiments 1-24, wherein the process is conducted in a fixed bed reactor, and wherein the olefin feedstock and the chemically-treated solid oxide are contacted at a WHSV in any range disclosed herein, e.g., from 0.05 to 10, from 0.05 to 5, from 0.1 to 3, or from 0.5 to 2.5.

Embodiment 26

The process defined in any one of embodiments 1-25, wherein a molar ratio of the aromatic compound to the olefin feedstock (aromatic:olefin) is in any molar ratio range disclosed herein, e.g., from 1:1 to 50:1, from 2:1 to 35:1, from 5:1 to 20:1, or from 7:1 to 17:1.

Embodiment 27

The process defined in any one of embodiments 1-26, wherein the olefin conversion or single pass conversion (moles consumed versus moles initially present) is in any range of conversions or single pass conversions disclosed herein, e.g., at least 50%, at least 80%, at least 90%, at least 95%, at least 98%, at least 99%, or 100%.

Embodiment 28

The process defined in any one of embodiments 1-27, wherein the product comprises a molar ratio of mono-alkylated aromatic compounds to multi-alkylated aromatic compounds (mono-alkylated:multi-alkylated) in any range disclosed herein, e.g., at least 1:1, at least 3:1, from 1:1 to 50:1, from 1.1:1 to 50:1, or from 1.2:1 to 25:1.

Embodiment 29

The process defined in any one of embodiments 1-28, wherein the product comprises any amount of olefin oligomers disclosed herein, e.g., less than or equal to 10 wt. %, less than or equal to 5 wt. %, less than or equal to 1 wt. %, or less than or equal to 0.1 wt. %, based on the total weight of the product.

Embodiment 30

The process defined in any one of embodiments 1-29, wherein the process further comprises a step of separating at least a portion of the chemically-treated solid oxide from the alkylated aromatic compound.

Embodiment 31 The process defined in embodiment 30, wherein the separating step is performed using any technique disclosed herein, e.g., filtration, evaporation, or distillation, as well as combinations thereof.

Embodiment 32

The process defined in any one of embodiments 1-29, wherein the process further comprises a step of isolating at least a portion of the alkylated aromatic compound from the chemically-treated solid oxide, and/or from the aromatic compound, and/or from the olefin feedstock.

Embodiment 33

The process defined in embodiment 32, wherein the isolating step is performed using any technique disclosed herein, e.g., filtration, evaporation, or distillation, as well as combinations thereof.

We claim:
1. A process for alkylating an aromatic compound, the process comprising:
    contacting the aromatic compound, an olefin feedstock, and a chemically-treated solid oxide at an alkylation temperature in a range from 0° C. to 60° C. to produce a product comprising an alkylated aromatic compound;
    wherein the chemically-treated solid oxide comprises a solid oxide treated with an electron-withdrawing anion, and the electron-withdrawing anion is at least on an exterior surface of the chemically-treated solid oxide.

2. The process of claim 1, wherein the aromatic compound comprises a $C_6$ to $C_{24}$ hydrocarbon aromatic compound.

3. The process of claim 1, wherein the aromatic compound comprises benzene, naphthalene, toluene, cumene, xylene, ethylbenzene, or any combination thereof.

4. The process of claim 1, wherein the olefin feedstock comprises at least 75 wt. % $C_3$ to $C_{18}$ alpha olefins.

5. The process of claim 1, wherein the olefin feedstock comprises a $C_2$ to $C_{40}$ alpha olefin.

6. The process of claim 1, wherein the olefin feedstock comprises ethylene, propylene, 1-butene, 1-pentene, 1-hexene, 1-octene, 1-decene, 1-dodecene, 1-tetradecene, 1-hexadecene, 1-octadecene, or any combination thereof.

7. The process of claim 1, wherein the alkylation temperature is in a range from 20° C. to 60° C.

8. The process of claim 1, wherein the solid oxide comprises silica, alumina, silica-alumina, silica-coated alumina, aluminum phosphate, aluminophosphate, heteropolytungstate, titania, silica-titania, zirconia, silica-zirconia, magnesia, boria, zinc oxide, any mixed oxide thereof, or any combination thereof.

9. The process of claim 1, wherein the electron-withdrawing anion comprises sulfate, fluoride, chloride, or any combination thereof.

10. The process of claim 1, wherein the chemically-treated solid oxide comprises a fluorided solid oxide and/or a sulfated solid oxide.

11. The process of claim 1, wherein the chemically-treated solid oxide comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof.

12. The process of claim 1, wherein the product comprises less than or equal to 1 wt. % olefin oligomers, based on the total weight of the product.

13. The process of claim 12, wherein:
    the aromatic compound comprises benzene, naphthalene, toluene, cumene, xylene, ethylbenzene, furan, pyridine, methylpyridine, or any combination thereof; and
    the olefin feedstock comprises ethylene, propylene, 1-butene, 1-pentene, 1-hexene, 1-octene, 1-decene, 1-dodecene, 1-tetradecene, 1-hexadecene, 1-octadecene, or any combination thereof.

14. The process of claim 1, wherein:
    a molar ratio of the aromatic compound to the olefin feedstock is in a range from 2:1 to 35:1;
    the process has an olefin conversion of at least 80%;
    the product comprises less than or equal to 5 wt. % olefin oligomers, based on the total weight of the product; and
    the product comprises a molar ratio of mono-alkylated aromatic compounds to multi-alkylated aromatic compounds in a range from 1.2:1 to 25:1.

15. The process of claim 14, wherein:
    the aromatic compound comprises benzene, naphthalene, toluene, cumene, xylene, ethylbenzene, furan, pyridine, methylpyridine, or any combination thereof; and
    the olefin feedstock comprises ethylene, propylene, 1-butene, 1-pentene, 1-hexene, 1-octene, 1-decene, 1-dodecene, 1-tetradecene, 1-hexadecene, 1-octadecene, or any combination thereof.

16. The process of claim 1, wherein:
a molar ratio of the aromatic compound to the olefin feedstock is in a range from 5:1 to 20:1;
the process has an olefin conversion of at least 90%;
the product comprises less than or equal to 1 wt. % olefin oligomers, based on the total weight of the product; and
the product comprises a molar ratio of mono-alkylated aromatic compounds to multi-alkylated aromatic compounds in a range from 3:1 to 25:1.

17. A process for alkylating an aromatic compound, the process comprising:
contacting the aromatic compound, an olefin feedstock, and a chemically-treated solid oxide at an alkylation temperature in a range from 0° C. to 60° C. to produce a product comprising an alkylated aromatic compound;
wherein the chemically-treated solid oxide comprises sulfated alumina, and sulfate is at least on an exterior surface of the sulfated alumina.

18. The process of claim 17, wherein the product comprises less than or equal to 1 wt. % olefin oligomers, based on the total weight of the product.

19. The process of claim 17, wherein:
the aromatic compound comprises benzene, naphthalene, toluene, cumene, xylene, ethylbenzene, furan, pyridine, methylpyridine, or any combination thereof; and
the olefin feedstock comprises ethylene, propylene, 1-butene, 1-pentene, 1-hexene, 1-octene, 1-decene, 1-dodecene, 1-tetradecene, 1-hexadecene, 1-octadecene, or any combination thereof.

20. The process of claim 19, wherein:
a molar ratio of the aromatic compound to the olefin feedstock is in a range from 2:1 to 35:1;
the process has an olefin conversion of at least 80%;
the product comprises less than or equal to 5 wt. % olefin oligomers, based on the total weight of the product; and
the product comprises a molar ratio of mono-alkylated aromatic compounds to multi-alkylated aromatic compounds in a range from 1.2:1 to 25:1.

21. The process of claim 19, wherein:
a molar ratio of the aromatic compound to the olefin feedstock is in a range from 5:1 to 20:1;
the process has an olefin conversion of at least 90%;
the product comprises less than or equal to 1 wt. % olefin oligomers, based on the total weight of the product; and
the product comprises a molar ratio of mono-alkylated aromatic compounds to multi-alkylated aromatic compounds in a range from 3:1 to 25:1.

* * * * *